(12) United States Patent
Zhang et al.

(10) Patent No.: US 6,646,005 B1
(45) Date of Patent: Nov. 11, 2003

(54) METHOD OF TREATING HAIR LOSS USING SULFONYL THYROMIMETIC COMPOUNDS

(75) Inventors: Lixin Lilly Zhang, Cincinnati, OH (US); Robert Scott Youngquist, Mason, OH (US)

(73) Assignee: The University of Texas Southwestern Medical Center, Dallas, TX (US)

( * ) Notice: Subject to any disclaimer, the term of this patent is extended or adjusted under 35 U.S.C. 154(b) by 0 days.

(21) Appl. No.: 09/980,351

(22) PCT Filed: Mar. 1, 2000

(86) PCT No.: PCT/US00/05199

§ 371 (c)(1), (2), (4) Date: Feb. 21, 2002

(87) PCT Pub. No.: WO00/72810

PCT Pub. Date: Dec. 7, 2000

Related U.S. Application Data

(60) Provisional application No. 60/137,023, filed on Jun. 1, 1999.

(51) Int. Cl.[7] .................. A61K 31/50; A61K 31/44; A61K 31/195; A61K 31/192

(52) U.S. Cl. .................. 514/562; 514/247; 514/347; 514/570

(58) Field of Search ................. 514/247, 347, 514/562, 570

(56) References Cited

U.S. PATENT DOCUMENTS

| | | | |
|---|---|---|---|
| 3,530,146 A | 9/1970 | Newman et al. | 260/330.5 |
| 3,616,237 A | 10/1971 | Newman et al. | 195/80 |
| 4,323,691 A | 4/1982 | Ours et al. | 560/36 |
| 4,425,404 A | 1/1984 | Suzuki et al. | 428/341 |
| 4,683,241 A | 7/1987 | Miyano et al. | 514/512 |
| 4,711,855 A | 12/1987 | Feinberg | 436/500 |
| 5,061,798 A | 10/1991 | Emmett et al. | 544/239 |
| 5,284,971 A | 2/1994 | Walker et al. | 562/429 |
| 5,401,772 A | 3/1995 | Yokoyama | 514/539 |
| 5,569,674 A | 10/1996 | Yokoyama et al. | 514/539 |
| 5,580,722 A | 12/1996 | Liechtfried et al. | 435/6 |
| 5,654,468 A | 8/1997 | Yokoyama et al. | 560/43 |
| 5,773,663 A | 6/1998 | Rehing et al. | 568/333 |
| 5,807,820 A | 9/1998 | Elias | 514/11 |
| 5,883,294 A | 3/1999 | Scanlan et al. | 562/471 |
| 6,174,925 B1 | 1/2001 | Bailey et al. | 514/646 |
| 6,221,911 B1 | 4/2001 | Lavin et al. | 514/567 |

FOREIGN PATENT DOCUMENTS

| | | |
|---|---|---|
| AT | 388372 | 6/1989 |
| CA | 1179269 | 12/1984 |

(List continued on next page.)

OTHER PUBLICATIONS

N Yokoyama: "Synthesis and structure–activity relationships of oxamic acid and acetic acid derivatives related to L–thronine" Journal of Medicinal Chemistry, US, American Chemical Society. Washington, vol. 38, No. 4, 1995, pp. 695–707.

Yamamoto et al., "Hair Growth–Stimulating Effects of Cyclosporin A and Fk506, Potent Immunosuppressants", Journal of Dermatologica Science, vol. 7 (suppl.), pp. S47–S54 (1994).

Maurer et al., "Hair Growth Modulation by Topical Immunophilin Ligands", American Journal of Pathology, vol. 150, No. 4, pp. 1433–1441 (Apr. 1997).

Pans et al., Hair Growth Control by Immunosuppression:, Archives of Dermatological Research, vol. 288, No. 7, pp. 408–410 (1996).

Pans et al., Cyclosporin A, PSC 833 and FK 506, but not Cyclosporin H and Rapamycin, Induce Anagen and Inhibit Catagen in Murine Skin, The Journal of Investigative Dermatology, vol. 101, No. 3, p. 420 (1993).

Pans et al., "Cyclosporin A, FK 506 and Related Drugs as Tools for Hair Research", Archives of Dermatological Research, vol. 285, Nos. 1–2, p. 80 (1993).

Traber et al., "Cyclosporins—New Analogues by Precursor Directed Biosyntheses", The Journal of Antibiotics, vol. 42, No. 4, pp. 5–597 (1989).

(List continued on next page.)

*Primary Examiner*—Phyllis G. Spivack
(74) *Attorney, Agent, or Firm*—Michael Best & Friedrich LLP

(57) ABSTRACT

Methods for treating hair loss using a composition including a compound having the following structure

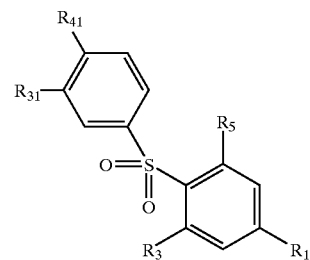

and pharmaceutically acceptable salts, hydrates, and biohydrolyzable amides, esters, and imides thereof are provided. $R_1$ is $-(CH_2)_n(CHNR_7R_8)_mC(O)R_9$, wherein n is an integer from 1 to 3, and m is an integer from 0 to 1. $R_3$ and $R_5$ each, independently, is chlorine, bromine, iodine and $-CH_3$. $R_7$ and $R_8$ each, independently, is hydrogen or C1 to C4 alkyl. $R_9$ is hydroxy, C1 to C4 alkoxy and $-NR_7R_8$. $R_{31}$ is a hydrogen, chlorine, bromine, iodine, C1 to C4 alkyl, C4 to C6 cycloalklyl, C1 to C4 haloalkyl, C4 to C6 halocycloalkyl, or $CH(R_{10})Ar$. Ar is 5-hydroxypyrid-2-yl, 6-hydroxypyrid-3-yl, 6-hydroxypyridazin-3-yl, 6-methioxypyridazin-3-yl N-oxide or 6-hydroxypyridazin-3-yl N-oxide. $R_{10}$ is hydrogen or C1 to C4 alkyl. $R_{41}$ is hydroxy or C1 to C4 alkoxy.

8 Claims, No Drawings

FOREIGN PATENT DOCUMENTS

| | | |
|---|---|---|
| DE | 1617477 | 1/1970 |
| DE | 2014514 | 10/1970 |
| DE | 4214363 | 11/1992 |
| DE | 4405469 | 8/1995 |
| EP | 51023 | 5/1982 |
| EP | 0123528 | 10/1984 |
| EP | 188248 | 7/1986 |
| EP | 243956 | 11/1987 |
| EP | 251315 | 1/1988 |
| EP | 0360701 | 3/1990 |
| EP | 0371484 | 6/1990 |
| EP | 0379935 | 8/1990 |
| EP | 0454165 | 10/1991 |
| EP | 498707 | 8/1992 |
| EP | 0580550 | 1/1994 |
| EP | 0749752 | 12/1996 |
| EP | 810218 | 12/1997 |
| FR | 2543434 | 10/1984 |
| FR | 2755 965 | 5/1998 |
| GB | 859546 | 10/1968 |
| GB | 2138286 | 10/1984 |
| JP | 59041343 | 3/1984 |
| JP | 61165311 | 7/1986 |
| JP | 62150245 | 7/1987 |
| JP | 63146845 | 6/1988 |
| JP | 63279246 | 11/1988 |
| JP | 2300148 | 12/1990 |
| JP | 4052646 | 2/1992 |
| JP | 04368379 | 12/1992 |
| JP | 4368379 | 12/1992 |
| JP | 6172340 | 6/1994 |
| JP | 7149614 | 6/1995 |
| JP | 8092082 | 4/1996 |
| JP | 8267922 | 10/1996 |
| JP | 8267932 | 10/1996 |
| JP | 8277243 | 10/1996 |
| JP | 10133427 | 5/1998 |
| JP | 10158382 | 6/1998 |
| PL | 119115 | 11/1981 |
| PL | 138940 | 11/1986 |
| WO | 9101379 | 2/1991 |
| WO | 9212635 | 8/1992 |
| WO | 9420062 | 9/1994 |
| WO | 96 25943 | 8/1996 |
| WO | 9707790 | 3/1997 |
| WO | 9857919 | 12/1998 |
| WO | 0000468 | 1/2000 |

OTHER PUBLICATIONS

Vinod K. Sharma et al. "Evaluation of thyroid function in North Indians with alopecia areta: Response to intravenous injection of 100microgram thyrotropin releasing hormone (TRH)", vol. 26, No. 6, pp. 339–342 (1999).
Berman, et al., Peripheral Effects of L–Thyroxine on Hair Growth and Coloration in Cattle, J. Endocrin 20: 288–292 (1960).
Gunaratnam, et al., The Journal of Small Animal Practice, (1986), pp. 17–29, vol. 27, No. 1.
Hale, et al., The Journal of Experimental Zoology, (1975), pp. 49–62, 191.
Lauer, et al., Chem. Ber. (1969), pp. 1631–1640, 102 (5).
Kamikura, Shokuhin Eiseigaku Zasshi (1968), pp. 348–357, 9 (5).
Atkinson, et al., J. Chem. Soc. C (1969), pp. 281–287, (2).
Chambers, et al., Tetrahedron (1969), pp. 565–572, 25 (3).
Segal, et al., J. Pharm. Sci. (1968), pp. 874–876, 57 (5).
Seikel, et al., Tetrahedron (1968), pp. 1475–1488, 24 (3).
Isaka, et al., Yakugaku Zasshi (1967), pp. 1288–1289, 87 (10).
Okuda, et al., Yakugaku Zasshi (1967), pp. 1003–1005, 87 (8).
Locksley, et al., Tetrahedron (1967), pp. 2229–2234, 23 (5).
Brown, Bull. Natl. Inst. Sci. India (1965), No. 31, pp. 167–178.
Koch, Angew. Makromol. Chem. (1971), pp. 21–33, 20.
Isaka, et al. Yakugaku Zasshi (1971), pp. 1027–1029, 91 (9).
Lubenets, et al., Zh. Org. Khim. (1971), pp. 805–812, 7 (4).
Newman, J. Heterocycl. Chem. (1970), pp. 957–958, 7 (4).
Lubenets, et al., Zh. Org. Khim. (1970), pp. 365–368, 6 (2).
Sargent, et al., J. Chem. Soc. C (1969), pp. 2763–2767, (19).
Findlay, et al., J. Chem. Soc. C (1969), pp. 2761–2762, (19).
Newman, J. Org. Chem. (1969), pp. 1463–1465, 34 (5).
Harris, J. Am. Chem. Soc. (1976), pp. 5380–5386, 98 (17).
Sargent, et al., Aust. J. Chem. (1976), pp. 907–914, 29 (4).
Chevolet–Magueur et al., Phytochemistry (1976), pp. 767–771, 15.
Holloway, et al., Phytochemistry (1975), pp. 2517–2518, 14 (11).
Owen, et al., J. Chem. Soc., Perkin Trans. 1 (1975) pp. 1380–1386, (14).
Kroeller, Mitteilungsbl. GDCH–Fachgruppe Lebensmittelchem. Gerichtl. Chem. (1975), pp. 181–182, 29 (5).
Ghosal et al., J. Chem. Soc., Perkin Trans. 1 (1974), pp. 2538–2541, (22).
Hassall, et al., J. Chem. Soc., Perkin Trans. 1 (1973), pp. 2853–2861, (23).
Sargent, Can. J. Chem. (1973), pp. 4088–4089, 51 (24).
Quillinan, et al., J. Chem. Soc., Perkin Trans. 1 (1973), pp. 1329–1337 (13).
Hendrickson, et al., J. Amer. Chem. Soc. (1972), pp. 6834–6843, 94 (19).
Sato, et al., Tennen Yuki Kagobutsu Toronkai Koen Yoshishu, 21st (1978), pp. 152–158; Publisher Hokkaido Daizku, Sapporo, Japan.
Sundholm, Tetrahedron (1978), pp. 577–586 34 (5).
Prashad, et al., Indian J. Chem., Sect. B (1978), pp. 142–143, 16B (2).
Sato, et al., J. Chem. Soc., Chem. Commun. (1978), pp. 135–136, (3).
Feringa, et al., Tetrahedron Lett. (1977), pp. 4447–4450, (50).
Djura, et al., J. Chem. Soc., Perkin Trans. 1 (1978), pp. 395–400, (4).
Broadhurst, et al., J. Chem. Soc., Perkin Trans. 1 (1977), pp. 2502–2512 (22).
Fujita, et al., Tetrahedron Lett. (1977), pp. 4503–4506, (51).
Schweppe, Mikrochim. Acta (1977), pp. 583–596 2 (5–6).
Ueda, et al., Bull. Chem. Soc. Jpn. (1977), pp. 193–196, 50 (1).
Sargent, et al., Aust. J. Chem. (1976), pp. 2263–2269, 29 (10).
Danilenko, et al., Izv. Akad. Nauk SSSR, Ser. Khim. (1980), pp. 1606–1611, (7).
Fujita, et al., Chem. Pharm. Bull. (1980), pp. 2482–2486, 28 (8).
Fitzpatrick, et al., J. Chem. Soc., Perkin Trans. 1 (1980), pp. 85–89, (1).
Sundholm, Acta Chem. Scand., Ser. B (1979), pp. 475–482, B33 (7).
Sato, et al., Symp. Pap.—IUPAC Int. Symp. Chem. Natl. Prod., 11th (1978), vol. 1, pp. 175–178.

Andreev, et al., Izv. Sib. Otd. Akad. Naul SSSR, Ser. Tekh. Nauk (1979), pp. 124–129, (2).
Baslas, et al., Curr. Sci. (1979), pp. 814–815, 48 (18).
Zharkova, et al., Rev. Phys. Appl. (1979), pp. 555–558, 14 (4).
Avnir, et al., J. Chem. Soc., Chem. Commun. (1978), pp. 1109–1110, (24).
Sala, et al., J. Chem. Soc., Chem. Commun. (1978), pp. 1043–1044, (23).
Feringa, et al., Bioorg. Chem. (1978), pp. 397–498, 7 (4).
Baslas, et al., Acta Cienc. Indica, [Ser.] Chem. (1981), pp. 31–34, 7 (1–4).
Sargent, J. Chem. Soc., Perkin Trans. 1 (1982), pp. 403–411, (2).
Cullen, et al., Aust. J. Chem. (1981), pp. 2701–2703, 34 (12).
Fujita, et al., Phytochemistry (1981), pp. 2183–2185, 20 (9).
Correa, et al., Phytochemistry (1981), pp. 305–307, 20 (2).
McEwen, et al., J. Chem. Soc., Perkin Trans. 1 (1981), pp. 883–886, (3).
Sala, et al., J. Chem. Soc., Perkin Trans 1 (1981), pp. 887–882, (3).
Finlay–Jones, et al., J. Chem. Soc., Perkin Trans. 1 (1981), pp. 874–876, (3).
Sala, et al., J. Chem. Soc., Perkin Trans. 1 (1981), pp. 855–869, (3).
Cotterill, et al., J. Chem. Soc., Perkin Transd. 1 (1980), pp. 2353–2357, (11).
Tanaka, et al., Chem. Pharm. Bull. (1984), pp. 2676–2686, 32 (7).
Dembri, et al., Mol. Cell. Endocrinol (1984), pp. 223–232, 37 (2).
Mahandru, et al., J. Chem. Soc., Perkin Trans. 1 (1983), pp. 413–416, (2).
Ruminski, Chem. Ber. (1983), pp. 970–979, 116 (3).
Cody, Acta Crystallogr, Sect. B (1982), B38 (8), 2270–2272.
Shapiro, et al., J. Protozool. (1982), pp. 85–90, 29 (1).
Malhotra, et al., Indian J. Chem., Sect. B (1982), pp. 107–108, 21B (2).
Comber, et al., J. Chem. Soc., Perkin Trans. 1 (1989), pp. 441–448, (3).
Sant'ana, et al., F.E.C.S. Int. Conf. Chem. Biotechnol. Biol. Act. Nat. Prod., [Proc.] 3rd (1987), Meeting Date 1985, vol. 4, pp. 363–366.
Gil, et al., J. Nat. Prod. (1988), pp. 339–343, 51 (2).
Sannicola, Gazz. Chim. Ital. (1985), pp. 91–95, 115 (2).
Kellman, et al., ACS Symp. Ser. (1987), 326 (Phase Transfer Catal.: New Chem., Catal., Appl.), pp. 128–142.
Fujii, et al., J. Biochem. (Tokyo) (1987), pp. 11–18, 101 (1).
Oda, et al., Chem. Pharm. Bull. (1986), pp. 858–863, 34 (2).
Gunzinger et al., Helv. Chim. Acta (1985), pp. 1940–1947, 68 (7).
Ahluwalia, et al., Monatsh. Chem. (1985), pp. 869–872, 116 (6–7).
Pulgarin, et al., Helv. Chim. Acta (1985), pp. 945–948, 68 (4).
Plattner, et al., Diuretics: Chem., Pharmacol., Clin. Appl., Proc. Int. Conf. Diuretics, 1st (1984), pp. 21–29.
Fletcher, et al., Organohalogen Compd. (1993), 12 (Dioxin '93, 13th International Symposium on Chlorinated Dioxins and Related Compounds, 1993), pp. 103–106.
Minami, et al., Phytochemistry (1994), pp. 501–506, 36 (2).
Lin, et al., J. Pharm. Sci. (1992), pp. 1109–1112, 81 (11).
Singh, et al., Pol. J. Chem. (1992), pp. 469–475, 66 (3).
Elix, et al., Aust. J. Chem. (1991), pp. 1157–1162, 44 (8).
Elix, et al., Aust. J. Chem. (1990), pp. 1591–1595, 43 (9).
Elix, et al., Aust. J. Chem. (1990), pp. 1291–1295, 43 (7).
Horne, et al., J. Org. Chem. (1990), pp. 4520–4522, 55 (15).
Birkbeck, et al., Aust. J. Chem. (1990), pp. 419–425, 43 (2).
Pulgarin, et al., Helv. Chim. Acta (1989), pp. 1061–1065, 72 (5).
Aurell, et al., J. Nat. Prod. (1989), pp. 852–857, 52 (4).
Vasilevskaya, et al., Zh. Org. Khim. (1970), pp. 126–132, 6 (1).
Yoshihara, et al., Bioorg. Med. Chem. (1998), pp. 1179–1183, 6 (8).
Dembri, et al., Mol. Cell. Endocrinol. (1984), pp. 223–232, 37 (2).
Cody, et al., Acta Crystallogr., Sect. B (1982), pp. 2270–2272, B38 (8).
Ito, et al., Chem. Pharm. Bull, (1997), pp. 1403–1413, 45 (9).
Mercer, et al., Polymer (1997), pp. 1989–1995, 38 (8).
Goodwin, et al., Macromolecules (1997), pp. 2767–2774, 30 (9).
Krumm, et al., Inorg. Chem. (1997), pp. 366–381, 36 (3).
Nishida, et al., Inorg. Chem. (1995), pp. 6085–6092, 34 (24).
Verma, et al., Nat. Prod. Lett. (1994), pp. 105–110, 5 (2).
Mehta, et al., Tetrahedron (1994), pp. 11729–11742, 50 (40).
Yoshihara, et al., Bioorg. Med. Chem. (1998), pp. 1179–1182, 6 (8).
Chiellini, et al., Chem. Biol. (1998), pp. 299–306, 5 (6).
Ji, et al., Yaoxue Xuebao (1998), pp. 72–74, 33 (1).
Krumm, et al., Inorg. Chem. (1997), pp. 5222–5230, 36 (23).
Kuroda, et al., Chem. Pharm. Bull, (1997), pp. 678–684, 45 (4).
Kuroda, et al., J. Org. Chem. (1996), pp. 9560–9563, 61 (26).
Iwasaki, et al., Chem. Pharm. Bull. (1995), pp. 1701–1705, 43 (10).
Yasuda, et al., Mokuzai Gakkaishi (1986), pp. 51–58, 32 (1).
Keay,, et al., Can. J. Chem. (1983), pp. 1987–1995, 61 (9).
Bogoslovskii, et al., Org. Khim. (1976), pp. 39–43. Gor'kogo, Perm. USSR.
Lapkin, et al., Zh. Org. Khim. (1972), pp. 292–293, 8 (2).

METHOD OF TREATING HAIR LOSS USING SULFONYL THYROMIMETIC COMPOUNDS

This application claims the benefit of Provisional Application Ser. No. 60/137,023 filed Jun. 1, 1999.

FIELD OF THE INVENTION

The present invention relates to methods for treating hair loss in mammals, including arresting and/or reversing hair loss and promoting hair growth.

BACKGROUND OF THE INVENTION

Hair loss is a common problem which occurs, for example, through natural processes or is often chemically promoted through the use of certain therapeutic drugs designed to alleviate conditions such as cancer. Often such hair loss is accompanied by lack of hair regrowth which causes partial or full baldness.

As is well-known in the art, hair growth occurs by a cycle of activity which involves alternating periods of growth and rest. This cycle is often divided into three main stages which are known as anagen, catagen, and telogen. Anagen is the growth phase of the cycle and may be characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. Wherein hair growth ceases, most of the hair follicles reside in telogen and anagen is not engaged, thus causing the onset of full or partial baldness.

There have been many attempts in the literature to invoke the regrowth of hair by, for example, the promotion or prolongation of anagen. Currently, there are two drugs approved by the United States Food and Drug Administration for the treatment of male pattern baldness: topical minoxidil (marketed as Rogaine® by Pharmacia & Upjohn), and oral finasteride (marketed as Propecia® by Merck & Co., Inc.). For several reasons, however, including safety concerns and or lack of efficacy, the search for efficacious hair growth inducers is ongoing.

Interestingly, it is known that the thyroid hormone known as thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman, "Peripheral Effects of L-Thyroxine on Hair Growth and Coloration in Cattle", *Journal of Endocrinology*, Vol. 20, pp. 282–292 (1960); and Gunaratnam, "The Effects of Thyroxine on Hair Growth in the Dog", *J. Small Anim. Pract.*, Vol. 27, pp. 17–29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences, Inc., published Aug. 29, 1996.

Unfortunately, however, administration of T3 and/or T4 to treat hair loss is not practicable because these thyroid hormones are also known to induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991. Surprisingly, however, the present inventors have discovered compounds which promote hair growth without inducing cardiotoxicity. Consistent with this discovery, but without intending to be limited by theory, the present inventors have surprisingly discovered that the compounds useful in the present invention interact strongly with hair-selective thyroid hormone receptors but interact less strongly, or not at all, with heart-selective hormone receptors. These unique properties are, of course, not shared with T3 and/or T4. Accordingly, the compounds described for use in the methods and compositions herein are cardiac-sparing compounds useful for treating hair loss, including arresting and/or reversing hair loss and promoting hair growth.

SUMMARY OF THE INVENTION

The present invention relates to methods for treating hair loss comprising administering a cardiac-sparing compound which has been found by the present inventors to be particularly useful for treating hair loss in mammals, including arresting and/or reversing hair loss and promoting hair growth. The compounds utilized in the present method have the structure:

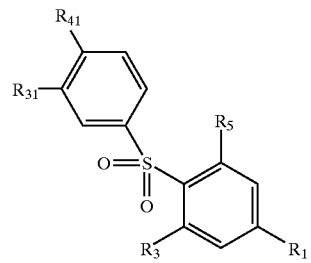

and pharmaceutically acceptable salts, hydrates, and biohydrolyzable amides, esters, and imides thereof, wherein $R_1$, $R_3$, $R_5$, $R_{31}$, and $R41$, are defined herein.

DETAILED DESCRIPTION OF THE INVENTION

The present invention relates to methods of using compounds and compositions which are particularly useful for treating hair loss in mammals, including arresting and/or reversing hair loss and promoting hair growth.

In addition to discovering that the present compounds are useful for treating hair loss, the present inventors have also surprisingly discovered that the preferred compounds are cardiac-sparing. The preferred compounds useful in the method of the present invention are therefore, as defined herein below, cardiac-sparing.

Publications and patents are referred to throughout this disclosure. All references cited herein are hereby incorporated by reference.

All percentages, ratios, and proportions used herein are by weight unless otherwise specified.

In the description of the invention various embodiments and/or individual features are disclosed. As will be apparent to the ordinarily skilled practitioner all combinations of such embodiments and features are possible and can result in preferred executions of the invention.

As used herein, wherein any variable, moiety, group, or the like occurs more than one time in any variable or structure, its definition at each occurrence is independent of its definition at every other occurrence.

Definition and Usage of Terms

The following is a list of definitions for terms used herein:

As used herein "salt" is a cationic salt formed at any acidic (e.g., carboxyl) group, or an anionic salt formed at any basic (e.g., amino) group. Many such salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). Such acceptable salts must, when administered, be appropriate for mammalian use.

As used herein, "alkoxy" is an oxygen radical having an alkyl substituent. Examples of alkoxy radicals include —O-methyl and —O-ethyl.

As used herein, "alkyl" is a saturated, straight or branched chain monovalent hydrocarbon radical. Unless otherwise specified, alkyls have from 1 to about 4 carbon atoms ($C_1$–$C_4$). Preferred alklyls include, for example, methyl, ethyl, propyl, iso-propyl, tert-butyl, n-butyl, sec-butyl, and iso-butyl.

As used herein, "biohydrolyzable amides" are amides of the compounds used in the present invention which do not interfere with the activity of the compound, or that are readily converted in vivo by a mammalian subject to yield an active compound.

As used herein, "biohydrolyzable esters" are esters of the compounds used in the present invention which do not interfere with the activity of the compound, or that are readily converted in vivo by a mammalian subject to yield an active compound.

As used herein, "biohydrolyzable imides" are imides of the compounds used in the present invention which do not interfere with the activity of the compound, or that are readily converted in vivo by a mammalian subject to yield an active compound.

As used herein, "carbocyclic ring", "carbocycle", or the like is a hydrocarbon ring radical. Carbocyclic rings are monocyclic or are fused, bridged, or spiro polycyclic rings. Unless otherwise specified, monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms. Carbocyclic rings (carbocycles) may be substituted or unsubstituted.

As used herein, "cycloalkyl" is a saturated carbocyclic ring radical having from four to six carbon atoms, such as cyclopentyl and cyclohexyl. Optionally, the cycloalkyl may be substituted with one or more alkyl groups.

As used herein, "haloalkyl" is an alkyl moiety substituted at one or more positions with a halogen radical.

As used herein, "halocycloalkyl" an cycloalkyl moiety substituted at one or more positions with a halogen radical.

As used herein "halogen" refers to chlorine, bromine, iodine, and fluorine, preferably chlorine, bromine, and iodine, more preferably chlorine and iodine, and most preferably iodine.

As used herein, "pharmaceutically acceptable" means suitable for use in a human or other mammal.

As used herein, "safe and effective amount of a compound" (or composition, or the like) means an amount that is effective to exhibit biological activity, preferably wherein the biological activity is arresting and/or reversing hair loss or promoting hair growth, at the site(s) of activity in a mammalian subject, without undue adverse side effects (such as toxicity, irritation, or allergic response), commensurate with a reasonable benefit/risk ratio when used in the manner of this invention.

Methods of the Present Invention

The present invention relates to methods of treating hair loss comprising administering a composition comprising a compound having the structure:

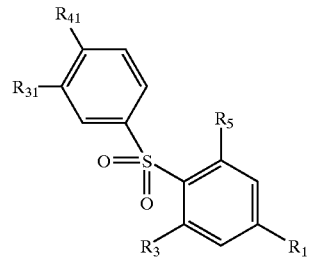

and pharmaceutically acceptable salts, hydrates, and biohydrolyzable amides, esters, and imides thereof, wherein:

(a) $R_1$ is —$(CH_2)_n(CHNR_7R_8)_mC(O)R_9$;

(b) n is an integer from 1 to 3;

(c) m is an integer from 0 to 1;

(d) $R_3$ and $R_5$ are each, independently, selected from the group consisting of chlorine, bromine, iodine, and —$CH_3$;

(e) $R_7$ and R8 are each, independently, selected from the group consisting of hydrogen and $C_1$–$C_4$ alkyl;

(f) $R_9$ is selected from the group consisting of hydroxy, $C_1$–$C_4$ alkoxy, and —$NR_7R_8$;

(g) $R_{31}$ is selected from the group consisting of hydrogen, chlorine, bromine, iodine, $C_1$–$C_4$ alkyl, $C_4$–$C_6$ cycloalkyl, $C_1$–$C_4$ haloalkyl, $C_4$–$C_6$ halocycloalkyl, and —$CH(R_{10})Ar$;

(h) Ar is selected from the group consisting of 5-hydroxypyrid-2-yl 6-hydroxypyrid-3-yl, 6-hydroxypyridazin-3-yl, 6-methoxypyridazin-3-yl N-oxide, and 6-hydroxypyridazin-3-yl N-oxide;

(i) $R_{10}$ is selected from the group consisting of hydrogen and $C_1$–$C_4$ alkyl; and (j) $R_{41}$ is selected from the group consisting of hydroxy and $C_1$–$C_4$ alkoxy.

The compounds useful in the method herein are further described in Walker et al., U.S. Pat. No. 5,284,971, assigned to Syntex, Inc., issued Feb. 8, 1994. However, for convenience, the compounds are more fully described herein below:

The $R_1$ Moiety

The $R_1$ moiety is —$(CH_2)_n(CHNR—R_8)_mC(O)R_9$.

The integer n is from 1 to 3. Preferably, n is 1 or 2. The integer m is either 0 or 1.

$R_7$ and $R_8$ are each, independently, selected from hydrogen and $C_1$–$C_4$ alkyl. Preferably, $R_7$ and $R_8$ are each hydrogen.

$R_9$ is selected from hydroxy, $C_1$–$C_4$ alkyl, and —$NR_7R_8$. As stated above, $R_7$ and $R_8$ are preferably each hydrogen.

Preferably, $R_1$ is an alkanoic or 2-aminoalkanoic acid radical derived from acetic acid, propionic acid, or 2-aminopropionic acid, or the methyl or ethyl ester thereof. As used herein, the term "alkanoic acid radical" refers to a monovalent carboxylic acid radical formed by removal of a hydrogen from the ω-carbon of an acid having from two to four carbon atoms, e.g., acetyl (—$CH_2COOH$), propionyl (—$CH_2CH_2COOH$), and butyryl (—$CH_2CH_2CH_2COOH$). As used herein, "aminoalkanoic acid radical" refers to a monovalent alkanoic acid radical having an amino or mono- or dialkylamino substituent on the α-carbon, e.g., 2-aminopropionyl (—$CH_2CH(NH_2)COOH$).

The $R_3$ and $R_5$ Moieties $R_3$ and $R_5$ are; each, independently, selected from chlorine, bromine, iodine, and —$CH_3$ (a methyl radical). Preferably, $R_3$ and $R_5$ are each, independently, selected from iodine and bromine. Most preferably $R_3$ and $R_5$ are either both bromine or both iodine.

The $R_{31}$ Moiety $R_{31}$ is selected from hydrogen, chlorine, bromine, iodine, $C_1$–$C_4$ alkyl, $C_4$–$C_6$ cycloalkyl, $C_1$–$C_4$ haloalkyl, $C_4$–$C_6$ halocycloalkyl, and —$CH(R_{10})Ar$.

Ar is selected from 5-hydroxypyrid-2-yl, 6-hydroxypyrid-3-yl, 6-hydroxypyridazin-3-yl, 6-methoxypyridazin-3-yl N-oxide, and 6-hydroxypyridazin-3-yl N-oxide. Preferably Ar is selected from 6-hydroxypyrid-3-yl, 6-hydroxypyridazin-3-yl, 6-methoxypyridazin-3-yl N-oxide, and 6-hydroxypyridazin-3-yl N-oxide.

$R_{10}$ is selected from hydrogen and $C_1$–$C_4$ alkyl.

Preferably, $R_{31}$ is selected from iodine, iso-propyl, cyclopentyl, cyclohexyl, and —$CH(R_{10})Ar$.

The $R_{41}$ Moiety $R_{41}$ is selected from hydroxy and $C_1$–$C_4$ alkoxy, preferably hydroxy. A preferred alkoxy for $R_{41}$ is methoxy.

Preferred Compounds Useful in the Present Invention

Preferred compounds useful in the methods and compositions of the present invention are:

(a) 3,5-dibromo4-(4-hydroxy-3-iodophenylsulfonyl)phenylacetic acid;

(b) 3,5-dibromo4-(3-iodo-4-methoxyphenylsulfonyl)phenylacetic acid;

(c) 3,5-dibromo4-(4-hydroxy-3-(6-methoxypyridazin-3-ylmethyl)phenylsulfonyl)phenylacetic acid;

(d) 3,5-dibromo4-(3-cyclohexyl4-hydroxyhenylsulfonyl)phenylacetic acid;

(e) 3,5-dibromo4-(3-cyclohexyl4-methoxyphenylsulfonyl)phenylacetic acid;

(f) 3,5-dibromo4-(3-cyclopentyl4-hydroxyphenylsulfonyl)phenylacetic acid;

(g) 3-(3,5-dibromo-4-(4-hydroxy-3-iso-propylphenylsulfonyl)phenyl)propionic acid;

(h) 2-amino-3-(3,5-dibromo4-(4-hydroxy-3-iso-propylphenylsulfonyl)phenyl)propionic acid;

(i) 3,5-dibromo4-(4-hydroxy-(6-hydroxypyridazin-3-ylmethyl)phenylsulfonyl)phenylacetic acid;

(j) 3,5-dibromo4-(4-hydroxy-3-iso-propylphenylsulfonyl)phenylacetic acid; and (k) 3,5-dibromo4-(3-iso-propyl)4-methoxyphenylsulfonyl)phenylacetic acid.

Of these, the most preferred compounds for use in the present invention are 3,5-dibromo4-(3-cyclohexyl4-hydroxyphenylsulfonyl)phenylacetic acid and 3,5-dibromo4-(3-cyclohexyl4-methoxyphenylsulfonyl)phenylacetic acid.

Analytical Methods

The present invention relates to methods of treating hair loss by administering a compound having a structure as described herein. Preferably, the compound utilized in the present invention will be cardiac-sparing. Compounds (test compounds) may be tested for their ability to induce anagen and their lack of cardiotoxicity (cardiac-sparing) using the following methods. Alternatively, other methods well-known in the art may be used (but with the term "cardiac-sparing" being defined according to the method disclosed herein below).

Cardiotoxicity Assay:

The cardiotoxicity assay measures the potential of a test compound to adversely affect the cardiovascular system. As thyroid hormone (T3) damages the cardiovascular system, the heart enlarges. See, e.g., Gomberg-Maitland et al., "Thyroid hormone and Cardiovascular Disease", *American Heart Journal*, Vol. 135(2), pp. 187–196 (1998); Klein and Ojamaa, "Thyroid Hormone and the Cardiovascular System", *Current Opinion in Endocrinology and Diabetes*, Vol. 4, pp.341–346 (1997); and Klemperer et al., "Thyroid Hormone Therapy and Cardiovascular Disease", *Progress in Cardiovascular Diseases*, Vol. 37 (4), pp. 329–336 (1996). This increases the weight of the heart relative to whole body weight. The cardiotoxicity assay herein below is used to test compounds for potentially adverse cardiac effects by measuring their effect on the heart-to-body weight ratio.

Two groups each of six male Sprague Dawley rats (Harlan Sprague Dawley, Inc., Indianapolis, Ind.) (each weighing from approximately 220 grams to 235 grams) are utilized. The first group is a vehicle control group and the second group is a test compound group. The length of the assay is 30 days, with treatment of vehicle or test compound in vehicle daily for 28 of those days as described below.

Prior to initiation of the assay, each rat is allowed to acclimate to standard environmental conditions for 5 days. Each rat receives food (standard rat chow diet) and water ad libitum 5 days prior to initiation of the assay as well as to termination of the study.

The vehicle is 91:9 (v:v) propylene glycol:ethanol. The test compound is prepared at a concentration of 500 µg/mL in the vehicle.

Each rat is weighed on day 1 of the assay. Dosage calculations are then performed: each rat will be administered daily a dosing solution of vehicle or test compound in vehicle (depending on whether the rat is in the vehicle control group or the test compound group, respectively) at 500 µL of dosing solution per kg of rat. For rats in the test compound group, this corresponds to a dose of 250 µg of test compound per kg of rat.

Day 2 is the first day of treatment with dosing solution for both groups. Body weights are taken for each rat on days 3, 5, 8, 10, 12, 15, 17, 19, 22, 24, 26, and 29 prior to dosing for that day; for each rat, the dosing solutions are recalculated and administered accordingly upon change in body weight.

Treatment occurs once daily in the morning on days 2 through 29, inclusive, for each rat in each group. For each treatment, the dosing solution is administered subcutaneously between the shoulders of the rat such that the injection sites are rotated in this area.

On day 30 in the morning, the rats of each group are euthanized with $CO_2$ from dry ice. Each rat is immediately weighed for total body weight.

The hearts of each rat are then excised as follows. An incision is made to expose the abdominal cavity. The rib cage is carefully cut at the sternum with small scissors, such that the heart and lungs are exposed. With small scissors and forceps, the vessels connected to the heart are cut away from the heart. These vessels include the caudal vena cava, left cranial vena cava (pulmonary trunk), right cranial vena cava, thoracic aorta, right subclavian artery, internal thoracic artery and vein, and any other small attachments. The heart is then immediately taken out intact, including the left and right auricles and left and right ventricles. Immediately thereafter, any excess tissue is trimmed away, the heart is lightly blotted on a paper towel until no more blood is visibly left behind on the paper towel, and the heart is weighed.

The heart weight is divided by the body weight after euthanization for each rat to give the heart/body ratio. The heart/body ratios for each rat in the vehicle control group are added together and divided by 6 (i.e., the total number of rats in the group) to give RV (ratio for vehicle control group). Similarly, the heart/body ratios for each rat in the test compound group are added together and divided by 6 to give RT (ratio for test compound group).

The index C is then calculated by dividing RT by RV. As defined herein, where C is less than 1.3, the test compound is cardiac-sparing. Preferably, C is less than 1.2, more preferably less than 1.15, and most preferably less than 1.1. In accordance with this method, T3 and T4 are not cardiac-sparing.

Telogen Conversion Assay:

The Telogen Conversion Assay measures the potential of a test compound to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein below is used to screen compounds for potential hair growth by measuring melanogenesis.

Three groups of 44 day-old C3H mice are utilized: a vehicle control group, a positive control group, and a test compound group, wherein the test compound group is administered a compound used in the method of the present invention. The length of the assay is at least 19 days with 15 treatment days (wherein the treatment days occur Mondays through Fridays). Day 1 is the first day of treatment. Most studies will end on Day 19, but a few may be carried out to Day 24 if the melanogenesis response looks positive, but occurs slowly. A typical study design is shown in Table 1 below. Typical dosage concentrations are set forth in Table 1, however the skilled artisan will readily understand that such concentrations may be modified.

TABLE 1

| Group # | Animal | Compound | Concentration | Application volume | Length of Study |
|---|---|---|---|---|---|
| 1 | 1–10 | Test Compound | 0.1% in vehicle** | 400 µL topical | 19 or 24 days |
| 2 | 11–20 | Positive Control (T3) | 0.01% in vehicle** | 400 µL topical | 19 or 24 days |
| 3 | 21–30 | Vehicle** | N/A | 400 µL topical | 19 or 24 days |

**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 2, the grades 0 to 4 represent the following visual observations as the skin progresses from white to bluish-black. Following this method, cyclosporin A typically receives a grade of 4 by day 19.

TABLE 2

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Method of Making

The compounds used in the methods of the present invention are prepared according to procedures which are well-known to those ordinarily skilled in the art. The starting materials used in preparing the compounds are known, made by known methods, or are commercially available as a starting material.

It is recognized that the ordinarily skilled artisan in the art of organic chemistry can readily carry out standard manipulations of organic compounds without further direction. Examples of such manipulations are discussed in standard texts such as J. March, *Advanced Organic Chemistry*, John Wiley & Sons (1992).

The ordinarily skilled artisan will readily appreciate that certain reactions are best carried out when other functionalities are masked or protected in the compound, thus increasing the yield of the reaction and/or avoiding any undesirable side reactions. Often, the artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons (1981).

The compounds of the present invention may have one or more chiral centers. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, may be separated using known methods, such as through the use of, for example, chiral salts and chiral chromatography.

In addition, it is recognized that one optical isomer, including a diastereomer and enantiomer, or a stereoisomer, may have favorable properties over the other. Thus, when disclosing and claiming the invention, when one racemic mixture is disclosed, it is clearly contemplated that both optical isomers, including diastereomers and enantiomers, or stereoisomers substantially free of the other are disclosed and claimed as well.

The syntheses of the compounds useful in the present invention are described in the art. Accordingly, the ordinarily skilled artisan will be able to prepare the compounds described herein. For further guidance, the syntheses of the present compounds are described in Walker et al., U.S. Pat. No. 5,284,971, assigned to Syntex, Inc., issued Feb. 8, 1994.

Use of the Present Compounds

The methods of the present invention are performed by administering to a mammal (preferably a human) a compound having a structure as described herein and, preferably, a pharmaceutically-acceptable or cosmetically-acceptable carrier.

The compounds herein may be used for the treatment of such conditions as treating hair loss in mammals, including arresting and/or reversing hair loss and promoting hair growth. Such conditions may manifest themselves in, for example, alopecia, including male pattern baldness and female pattern baldness.

Preferably the compounds of the present invention are, as defined herein, cardiac-sparing.

Preferably, in the methods of the present invention, the compounds are formulated into pharmaceutical or cosmetic compositions for use in treatment or prophylaxis of conditions such as the foregoing. Standard pharmaceutical formulation techniques are used, such as those disclosed in *Remington's Pharmaceutical Sciences*, Mack Publishing Company, Easton, Pa. (1990).

Typically, from about 5 mg to about 3000 mg, more preferably from about 5 mg to about 1000 mg, more preferably from about 10 mg to about 100 mg, of a compound having a structure as described herein is administered per day for systemic administration. It is understood that these dosage ranges are by way of example only, and that daily administration can be adjusted depending on various factors. The specific dosage of the compound to be administered, as well as the duration of treatment, and whether the treatment is topical or systemic are interdependent. The dosage and treatment regimen will also depend upon such factors as the specific compound used, the treatment indication, the efficacy of the compound, the personal attributes of the subject (such as, for example, weight, age, sex, and medical condition of the subject), compliance with the treatment regimen, and the presence and severity of any side effects of the treatment.

According to the present invention, the subject compounds are co-administered with a pharmaceutically-acceptable or cosmetically-acceptable carrier (herein collectively described as "carrier"). The term "carrier", as used herein, means one or more compatible solid or liquid filler diluents or encapsulating substances which are suitable for administration to a mammal. The term "compatible", as used herein, means that the components, of the composition are capable of being commingled with a compound of the present invention, and with each other, in a manner such that there is no interaction which would substantially reduce the efficacy of the composition under ordinary use situations. Carriers must, of course, be of sufficiently high purity and sufficiently low toxicity to render them suitable for administration to the animal, preferably mammal (most preferably human), being treated. The carrier can itself be inert or it can possess pharmaceutical and/or cosmetic benefits of its own.

The compositions of this invention may be in any of a variety of forms, suitable (for example) for oral, rectal, topical, nasal, ocular or parenteral administration. Of these, topical and/or oral administration are especially preferred with topical being most preferred. Depending upon the particular route of administration desired, a variety of carriers well-known in the art may be used. These include solid or liquid fillers, diluents, hydrotropes, surface-active agents, and encapsulating substances. Optional pharmaceutically-active or cosmetically-active materials may be included which do not substantially interfere with the activity of the compound of the present invention. The amount of carrier employed in conjunction with the compound is sufficient to provide a practical quantity of material for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Some examples of substances which can serve as carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate;. vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate: coloring agents; flavoring agents; tableting agents, stabilizers; antioxidants; preservatives; pyrogen-free water; isotonic saline; and phosphate buffer solutions.

The choice of a carrier to be used in conjunction with the subject compound is typically determined by the way the compound is to be administered.

In particular, carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the carrier, in compositions for parenteral administration, comprises at least about 90% by weight of the total composition.

Various oral dosage forms can be used, including Such solid forms as tablets, capsules, granules and bulk powders. These oral forms comprise a safe and effective amount, usually at least about 5%, and preferably from about 25% to about 50%, of a compound used in the present invention. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The carriers suitable for the preparation of unit dosage forms for oral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components depends on secondary considerations like taste, cost, and shelf stability, which are not critical for the purposes of the subject invention, and can be readily made by a person skilled in the art.

Orally administered compositions also include liquid solutions, emulsions, suspensions, powders, granules, elixirs, tinctures, syrups, and the like. The carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compounds of the present invention may also be topically administered. The carrier of the topical composition preferably aids penetration of the present compounds into the skin to reach the environment of the hair follicle. Topical compositions of the present invention may be in any form including, for example, solutions, oils, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl paimitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene; glycol monoethyl ether, dimethyl sulphoxide, dimethyl formamide, tetrahydrofuran; humectants, such as. glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds used in the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds utilizes liposomes such as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404–407 (1993); Wallach and Philippot, "New Type of Lipid Vesicle: Novasomet®", Liposome Technology, Vol. 1, pp. 141–156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The compounds of the present invention may also be administered by iontophoresis. See, e.g., internet site www.unipr.it/arpa/dipfarm/erasmus/erasm14.html; Banga et al., "Hydrogel-based Iontotherapeutic Delivery Devices for Transdermal Delivery of Peptide/Protein Drugs", Pharm. Res., Vol. 10 (5) pp. 697–702 (1993); Ferry, "Theoretical Model of Iontophoresis Utilized in Transdermal Drug Delivery", Pharmaceutical Acta Helvetiae, Vol 70, pp. 279–287 (1995); Gangarosa et al., "Modern Iontophoresis for Local Drug Delivery", Int. J. Pharm, Vol. 123, pp. 159–171 (1995); Green et al., "Iontophoretic Delivery of a Series of Tripeptides Across the Skin in vitro", Pharm. Res., Vol 8, pp. 1121–1127 (1991); Jadoul et al., "Quantification and Localization of Fentanyl and TRH Delivered by Iontophoresis in the Skin", Int. J Pharm., Vol. 120, pp. 221–8 (1995); O'Brien et al., "An Updated Review of its Antiviral Activity, Pharmacokinetic Properties and Therapeutic Efficacy", Drugs, Vol. 37, pp. 233–309 (1989); Parry et al., "Acyclovir Bioavailability in Human Skin", J. Invest. Dermatol., Vol. 98 (6), pp. 856–63 (1992); Santi et al., "Drug Reservoir Composition and Transport of Salmon Calcitonin in Transdermal Iontophoresis", Pharm. Res., Vol 14 (1), pp. 63–66 (1997); Santi et al., "Reverse Iontophoresis—Parameters Determining Electroosmotic Flow: I. pH and Ionic Strength", J. Control. Release, Vol. 3.8, pp. 159–165 (1996); Santi et al., "Reverse Iontophoresis—Parameters Determining Electroosmotic Flow: II. Electrode Chamber Formulation", J. Control. Release, Vol. 42, pp. 29–36 (1996); Rao et al. "Reverse Iontophoresis: Noninvasive Glucose Monitoring in vivo in Humans", Pharm. Res., Vol. 12 (12), pp. 1869–1873 (1995); Thysman et al., "Human Calcitonin Delivery in Rats by Iontophoresis", J. Pharm. Pharmacol., Vol. 46, pp. 725–730 (1994); and Volpato et al., "Iontophoresis Enhances the Transport of Acyclovir through Nude Mouse Skin by Electrorepulsion and Electroosmosis", Pharm. Res., Vol. 12 (11), pp. 1623–1627 (1995).

The compositions used in the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers.

Non-limiting examples of other hair growth stimulants which may be used in the compositions herein, including both systemic and topical compositions, include, for example, benzalkonium chloride, benzethonium chloride, phenol, estradiol, diphenhydramine hydrochloride, chlorpheniramine maleate; chlorophyllin derivatives, cholesterol, salicylic acid, cysteine, methionine, red pepper tincture, benzyl nicotinate, D,L-menthol, peppermint oil, calcium pantothenate, panthenol, castor oil, hinokitiol, prednisolone, resorcinol, monosaccharides and esterified monosaccharides, chemical activators of protein kinase C enzymes, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, and, of course, minoxidil or finasteride. The most preferred activity enhancers are minoxidil and finasteride, most preferably minoxidil.

Non-limiting examples of penetration enhancers which may be used in the compositions herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate; di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic, acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, and, 1 -dodecylazacyloheptan-2-one.

In all of the foregoing, of course, the compounds used in the present methods can be administered alone or as mixtures, and the compositions may further include additional drugs or excipients as appropriate for the indication.

The present invention further relates to kits comprising a compound and/or composition herein and information and/or instructions by words, pictures, and/or the like, that use of the kit will provide treatment for hair loss in mammals (particularly humans) including, for example, arresting and/or reversing hair loss and or promoting hair growth. In addition or in the alternative, the kit may comprise a compound and/or composition herein and information and/or instructions regarding methods of application of the compound and/or composition, preferably with the benefit of treating hair loss in mammals.

EXAMPLES OF COMPOSITION ADMINISTRATION

The following examples do not limit the invention, but provide guidance to the skilled artisan to perform the methods of the present invention. In each example, a compound other than the one mentioned may be substituted in the example by another having a structure as described herein with similar results.

Example A

A composition for topical administration is made, comprising:

| Component | Amount |
|---|---|
| 3,5-dibromo-4-(3-cyclohexl-4-hydroxyphenylsulfonyl)phenylacetic acid | 5% |
| Ethanol | 57% |
| Propylene Glycol | 19% |
| Dimethyl Isosorbide | 19% |

A human male subject suffering from male pattern baldness is treated by a method of this invention. Specifically, for 6 weeks, the above composition is daily administered topically to the subject.

Example B

A composition for topical administration is made according to the method of Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404–407 (1993), using 3,5-dibromo4-(3-cyclohexyl4-methoxyphenylsulfonyl)phenylacetic acid in lieu of cyclosporin A and using the Novasome 1 for the non-ionic liposomal formulation.

A human male subject suffering from male pattern baldness is treated each day with the above composition. Specifically, for 6 weeks, the above composition is administered topically to the subject.

Example C

A shampoo is made, comprising:

| Component | Ex. C-1 | Ex. C-2 | Ex. C-3 | Ex. C-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Gycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| 3,5-bromo-4-(3-iodo-4-methoxyphenylsulfonyl)phenylacetic acid | 2% | — | 3% | — |
| 3,5-bromo-4-(3-cyclopentyl-4-hydroxyphenylsulfonyl)phenylacetic acid | — | 1% | — | 7% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

A human subject suffering from male pattern baldness is treated by a method of this invention. Specifically, for 12 weeks, the above shampoo is used daily by the subject.

What is claimed is:

1. A method of treating hair loss comprising administering a composition comprising a cardiac-sparing compound characterized by the structure:

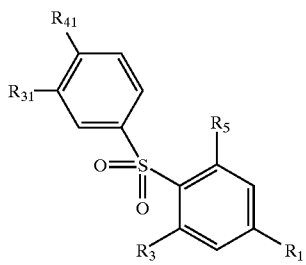

and pharmaceutically acceptable salts, hydrates, and biohydrolyzable amides, esters, and imides thereof, wherein:

$R_1$ is —$(CH_2)_n(CHNR_7R_8)_mC(O)R_9$;

n is an integer from 1 to 3;

m is an integer from 0 to 1;

$R_3$ and $R_5$ are each, independently, selected from the group consisting of chlorine, bromine, iodine, and —$CH_3$;

$R_7$ and $R_8$ are each, independently, selected from the group consisting of hydrogen and $C_1$–$C_4$ alkyl;

$R_9$ is selected from the group consisting of hydroxy, $C_1$–$C_4$ alkoxy, and —$NR_7R_8$;

$R_{31}$ is selected from the group consisting of hydrogen, chlorine, bromine, iodine, $C_1$–$C_4$ alkyl, $C_4$–$C_6$ cycloalkyl, $C_1$–$C_4$ haloalkyl, $C_4$–$C_6$ halocycloalkyl, and —$CH(R_{10})Ar$;

Ar is selected from the group consisting of 5-hydroxypyrid-2-yl, 6-hydroxypyrid-3-yl, 6-hydroxypyridazin-3-yl, 6-methoxypyridazin-3-yl N-oxide, and 6-hydroxypyridazin-3-yl N-oxide;

$R_{10}$ is selected from the group consisting of hydrogen and $C_1$–$C_4$ alkyl; and R4, is selected from the group consisting of hydroxy and $C_1$–$C_4$ alkoxy.

2. A method according to claim 1 wherein:

$R_1$ is —$(CH_2)_n(CH_2NH_2)_mC(O)R_9$;

n is an integer from 1 to 2;

$R_3$ and $R_5$ are each, independently, selected from the group consisting of chlorine, bromine, and iodine;

$R_9$ is selected from the group consisting of hydroxy, $C_1$–$C_4$ alkoxy, and $NH_2$;

$R_{31}$ is selected from the group consisting of hydrogen, chlorine, bromine, iodine, $C_1$–$C_4$ alkyl, $C_4$–$C_6$ cycloalkyl, and —$CH_2Ar$; and Ar is selected from the group consisting of 6-hydroxypyrid-3-yl, 6-hydroxypyridazin-3-yl, 6-methoxypyridazin-3-yl N-oxide, and 6-hydroxypyridazin-3-yl N-oxide.

3. A method according to claim 1 wherein:

$R_1$ is selected from the group consisting of an alkanoic radical derived from an acid and an 2-aminoalkanoic acid radical derived from the acid, wherein the acid is selected from the group consisting of acetic acid, propionic acid, 2-aminopropionic acid, and methyl- and ethyl-esters thereof, $R_3$ and $R_5$ are the same, and are selected from the group consisting of bromine and iodine; and $R_{31}$ is selected from the group consisting of iodine, isopropyl, cyclopentyl, cyclohexyl, and —$CH_2Ar$; and $R_{41}$, is selected from the group consisting of hydroxy, methoxy, and ethoxy.

4. A method according to claim 1 wherein the compound is selected from the group consisting of:

3,5-dibromo-4-(4-hydroxy-3-iodophenylsulfonyl) phenylacetic acid;

3,5-dibromo-4-(3-iodo-4-methoxyphenylsulfonyl) phenylacetic acid;

3,5-dibromo-4-(4-hydroxy-3-(6-methoxypyridazin-3-ylmethyl)phenylsulfonyl)phenylacetic acid;

3,5-dibromo-4-(3-cyclohexyl-4-hydroxyphenylsulfonyl) phenylacetic acid;

3,5-dibromo-4-(3-cyclohexyl-4-methoxyphenylsulfonyl) phenylacetic acid;

3,5-dibromo-4-(3-cyclopentyl-4-hydroxyphenylsulfonyl) phenylacetic acid;

3-(3,5-dibromo-4-(4-hydroxy-3-isopropylphenylsulfonyl)phenyl)propionic acid;

2-amino-3-(3,5-dibromo-4-(4-hydroxy-3-isopropylphenylsulfonyl)phenyl)propionic acid;

3,5-dibromo-4-(4-hydroxy-(6-hydroxypyridazin-3-ylmethyl) phenylsulfonyl) phenylacetic acid;

3,5-dibromo-4-(4-hydroxy-3-iso-propylphenylsulfonyl) phenylacetic acid; and 3,5-dibromo-4-(3-iso-propyl)-4-methoxyphenylsulfonyl) phenylacetic acid.

5. A method according to claim 1 wherein the compound is selected from the group consisting of:

3,5-dibromo-4-(3-cyclohexyl-4-hydroxyphenylsulfonyl) phenylacetic acid; and 3,5-dibromo-4-(3-cyclohexyl-4-methoxyphenylsulfonyl) phenylacetic acid.

6. A method according to claim 1 wherein the administration is topical.

7. A method according to claim 1 wherein the administration is oral.

8. A method according to claim 1 wherein the composition further comprises minoxidil.

* * * * *